US012672760B2

(12) United States Patent　　　(10) Patent No.:　US 12,672,760 B2
　　　Kuwae　　　　　　　　　　　　(45) Date of Patent:　　Jul. 7, 2026

---

(54) ENDOSCOPE

(71) Applicant: FUJIFILM Corporation, Tokyo (JP)

(72) Inventor: Toshiharu Kuwae, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 300 days.

(21) Appl. No.: 18/366,640

(22) Filed: Aug. 7, 2023

(65) Prior Publication Data

US 2024/0065529 A1　　Feb. 29, 2024

(30) Foreign Application Priority Data

Aug. 25, 2022　　(JP) ................................. 2022-134105

(51) Int. Cl.
A61B 1/00　　　　(2006.01)
A61B 1/005　　　(2006.01)
(52) U.S. Cl.
CPC ...... A61B 1/00096 (2013.01); A61B 1/00042 (2022.02); A61B 1/0052 (2013.01)
(58) Field of Classification Search
CPC ............ A61B 1/00096; A61B 1/00066; A61B 1/00188; A61B 1/00121; A61B 1/00128; A61B 1/00163; A61B 1/045; A61B 1/00042; A61B 1/0057; A61B 1/00064; A61B 1/00071; A61B 1/00119; A61B 1/0019; A61B 1/04; A61B 1/055; A61B 1/05; A61B 1/00098; A61B 1/00101; G02B 7/04; G02B 23/2476; G02B 23/2438
USPC ......... 600/167–168, 173–175, 160, 106–107
See application file for complete search history.

(56) References Cited

U.S. PATENT DOCUMENTS

| | | | |
|---|---|---|---|
| 2001/0018552 A1 | 8/2001 | Akiba | |
| 2013/0222563 A1* | 8/2013 | Kitano | ...................... H04N 7/18 348/65 |
| 2016/0015254 A1* | 1/2016 | Iwasaka | ............. A61B 1/00154 600/103 |
| 2016/0353974 A1* | 12/2016 | Kakehashi | ........... A61B 1/0055 |

(Continued)

FOREIGN PATENT DOCUMENTS

| | | |
|---|---|---|
| EP | 3123919 | 2/2017 |
| JP | H10108828 | 4/1998 |
| JP | H11326783 | 11/1999 |

(Continued)

OTHER PUBLICATIONS

"Search Report of Europe Counterpart Application", issued on Dec. 14, 2023, pp. 1-8.

(Continued)

*Primary Examiner* — Ryan N Henderson
*Assistant Examiner* — Pamela F Wu
(74) *Attorney, Agent, or Firm* — JCIPRNET

(57) ABSTRACT

An endoscope includes a movable lens group that is movable forward and backward in an optical axis direction, a flexible shaft that has a shaft axis, is configured to rotate in a rotation direction about the shaft axis, and moves the movable lens group in the optical axis direction in a case in which the flexible shaft rotates in the rotation direction, a zoom operation knob, a slider that moves forward and backward in a direction of the shaft axis according to an operation of the zoom operation knob, and a power conversion transmission mechanism that rotates the flexible shaft by the forward and backward movement of the slider.

7 Claims, 12 Drawing Sheets

(56)         References Cited

U.S. PATENT DOCUMENTS

2023/0107823 A1      4/2023    Amino

FOREIGN PATENT DOCUMENTS

| | | |
|---|---|---|
| JP | 2000147356 | 5/2000 |
| JP | 2000232603 | 8/2000 |
| JP | 2000267016 | 9/2000 |
| JP | 2001166225 | 6/2001 |
| JP | 2013172908 | 9/2013 |
| JP | 2022118349 | 8/2022 |
| WO | 2015163019 | 10/2015 |

OTHER PUBLICATIONS

"Notice of Resons for Refusal of Japan Counterpart Application", issued on Feb. 3, 2026, with English translation thereof, pp. 1-7.

* cited by examiner

FIG. 9

ENDOSCOPE

CROSS-REFERENCE TO RELATED APPLICATION

The present application claims priority under 35 U.S.C § 119(a) to Japanese Patent Application No. 2022-134105 filed on Aug. 25, 2022, which is hereby expressly incorporated by reference, in its entirety, into the present application.

BACKGROUND OF THE INVENTION

1. Field of the Invention

The present invention relates to an endoscope, and particularly relates to an endoscope comprising a zoom operation mechanism for moving a distal end optical system provided on a distal end side of an insertion part forward and backward in an optical axis direction.

2. Description of the Related Art

In general, an endoscope comprises an elongated insertion part to be inserted into a body and a hand operating part connected to a base end side of the insertion part. The insertion part includes a distal end optical system on a distal end side, and displays an observation image of a subject captured from the distal end optical system on a display device, such as a monitor.

JP1998-108828A (JP-H10-108828A) discloses an endoscope that performs focus adjustment by moving an objective lens forward and backward in an optical axis direction. With this endoscope, the objective lens is moved forward and backward in the optical axis direction by operating a focus adjustment knob of the hand operating part is to rotate a flexible shaft, converting the rotational movement into linear movement by a feed screw mechanism, and transmitting the converted linear movement to a lens frame.

Further, an endoscope disclosed in JP2001-166225A moves a movable lens forward and backward in an optical axis direction by rotating a linear transmitting member by the power of a motor, converting the rotational movement into the linear movement by a feed screw mechanism, and transmitting the converted linear movement to a lens frame.

SUMMARY OF THE INVENTION

Since the endoscope disclosed in JP1998-108828A (JP-H10-108828A) is an apparatus that moves the lens forward and backward by manually operating the focus adjustment knob, there is an advantage that costs (manufacturing cost and running cost) can be reduced as compared with the endoscope disclosed in JP2001-166225A that moves the lens forward and backward by the motor. However, JP1998-108828A (JP-H10-108828A) does not describe any zoom operation mechanism for efficiently transmitting an operation force of the focus adjustment knob to the shaft. That is, JP1998-108828A (JP-H10-108828A) does not disclose at all the zoom operation mechanism for efficiently moving the distal end optical system forward and backward in the optical axis direction.

The present invention has been made in view of such circumstances, and is to provide an endoscope comprising a zoom operation mechanism that can efficiently move a distal end optical system forward and backward in an optical axis direction.

An aspect of the present invention relates to an endoscope comprising a distal end optical system that is movable forward and backward in an optical axis direction, a shaft that has a shaft axis, is configured to rotate in a rotation direction about the shaft axis, and moves the distal end optical system in the optical axis direction in a case in which the shaft rotates in the rotation direction, an operation member, a slider that moves forward and backward in a direction of the shaft axis according to an operation of the operation member, and a power conversion transmission mechanism that rotates the shaft by the forward and backward movement of the slider.

According to the aspect of the present invention, it is preferable that the operation member is a rotational operation member configured to be rotationally operated, and the endoscope further comprises a swing member that swings in a case in which the rotational operation member is rotationally operated, and a link member that links the swing member with the slider and moves the slider forward and backward in a direction of the shaft axis in a case in which the swing member swings.

According to the aspect of the present invention, it is preferable that the power conversion transmission mechanism includes an engagement member provided on the slider, and a shaft member that is linked with the shaft and is formed with a spiral engaged part, on an outer peripheral surface, with which the engagement member is engaged, and the shaft member rotates in the rotation direction about the shaft axis by linear movement of the engagement member accompanied by the forward and backward movement of the slider.

According to the aspect of the present invention, it is preferable that the engagement member is a nut including a female screw, and the shaft member is a screw shaft including a male screw which is the engaged part.

According to the aspect of the present invention, it is preferable that the engagement member is a cam pin, and the shaft member is a cam shaft including a cam groove which is the engaged part.

According to the aspect of the present invention, it is preferable that the endoscope further comprises a rotation detection unit that detects a rotation angle of the shaft.

According to the aspect of the present invention, it is preferable that the endoscope further comprises an insertion part, and a hand operating part that is connected to a base end side of the insertion part, in which the operation member, the slider, and the power conversion transmission mechanism are provided on the hand operating part, the shaft is provided from the hand operating part to the insertion part, and the distal end optical system is provided on a distal end side of the insertion part.

According to the aspect of the present invention, it is preferable that the operation member is a rotational operation member configured to be rotationally operated, a bending operation knob that performs a bending operation of the insertion part is provided to be rotationally operated, on the hand operating part, and a rotation axis of the rotational operation member is disposed coaxially with a rotation axis of the bending operation knob.

According to the present invention, the distal end optical system can be efficiently moved forward and backward in the optical axis direction.

BRIEF DESCRIPTION OF THE DRAWINGS

FIG. 9 is an explanatory diagram showing a configuration of a zoom operation mechanism according to a second embodiment.

DESCRIPTION OF THE PREFERRED EMBODIMENTS

Figure 1:
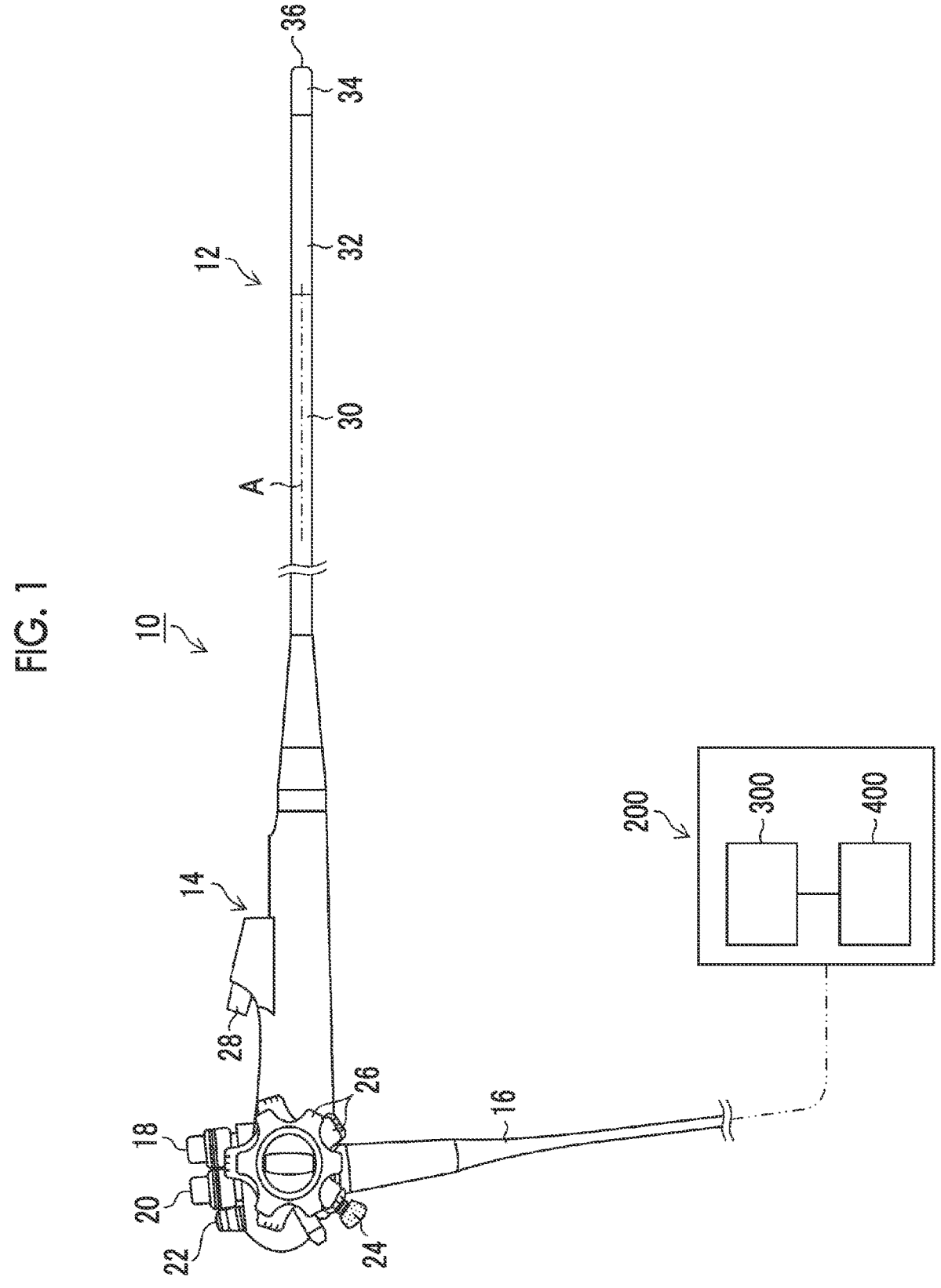
FIG. 1 is an overall configuration diagram of an endoscope according to an embodiment.

Hereinafter, embodiments of an endoscope according to the present invention will be described with reference to the accompanying drawings. FIG. 1 is an overall configuration diagram of an endoscope 10 according to the embodiment.

As shown in FIG. 1, the endoscope 10 comprises an insertion part 12 and a hand operating part 14 to which a base end side of the insertion part 12 is connected. A base end of a universal cable 16 is connected to the hand operating part 14. A connector device (not shown) connected to a processor device 200 is provided at the distal end of the universal cable 16. The processor device 200 comprises a light source device 300 and an image processing device 400. The light source device 300 comprises a processor-side connector (not shown) to which the connector device is connected. In addition, a display (not shown) that displays an image processed by the image processing device 400 is connected to the image processing device 400. An endoscope system of the present example comprising the endoscope 10 and the processor device 200 has a configuration in which the power, the light signal, or the like is transmitted in a noncontact manner between the endoscope 10 and the processor device 200 via the connector portion composed of the connector device and the processor-side connector.

The hand operating part 14 is provided with an air supply/water supply button 18, a suction button 20, a shutter button 22, a zoom operation knob 24, a pair of bending operation knobs 26, and a forceps insertion part 28 at predetermined positions, respectively.

The insertion part 12 has a longitudinal axis A, and includes a soft portion 30, a bendable portion 32, and a distal end hard portion 34 from the base end side toward a distal end side. The bending operation is performed on the bendable portion 32 remotely by rotationally operating the pair of bending operation knobs 26 provided on the hand operating part 14. As a result, a distal end surface 36 of the distal end hard portion 34 can be directed in a desired direction.

Figure 2:
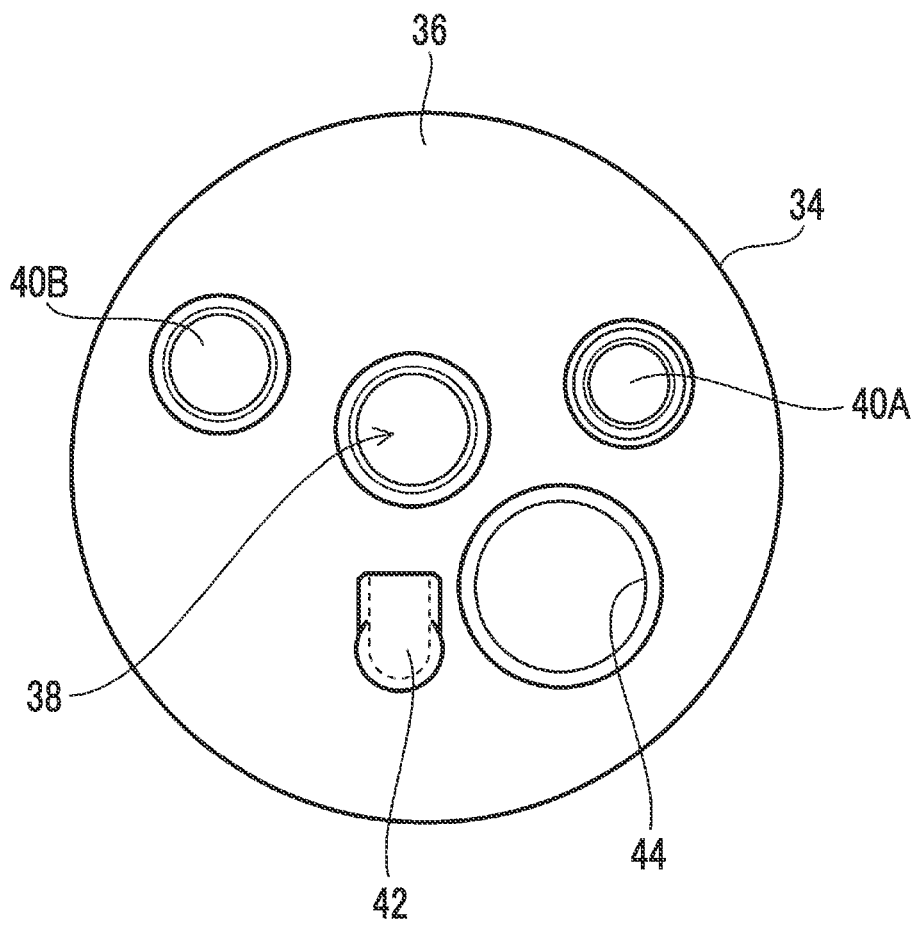
FIG. 2 is a front view of a distal end surface of a distal end hard portion.

FIG. 2 is a front view of the distal end surface 36 of the distal end hard portion 34. As shown in FIG. 2, on the distal end surface 36 of the distal end hard portion 34, an observation window 38, a pair of illumination windows 40A and 40B, an air supply/water supply nozzle 42, and a forceps port 44 are arranged at predetermined positions, respectively. As an example, the observation window 38 is disposed substantially in the center of the distal end surface 36, and the illumination windows 40A and 40B are arranged on both sides of the observation window 38. In addition, the air supply/water supply nozzle 42 is arranged toward the observation window 38, and the forceps port 44 is arranged in a space surrounded by the observation window 38, the illumination window 40A, and the air supply/water supply nozzle 42.

Figure 3:
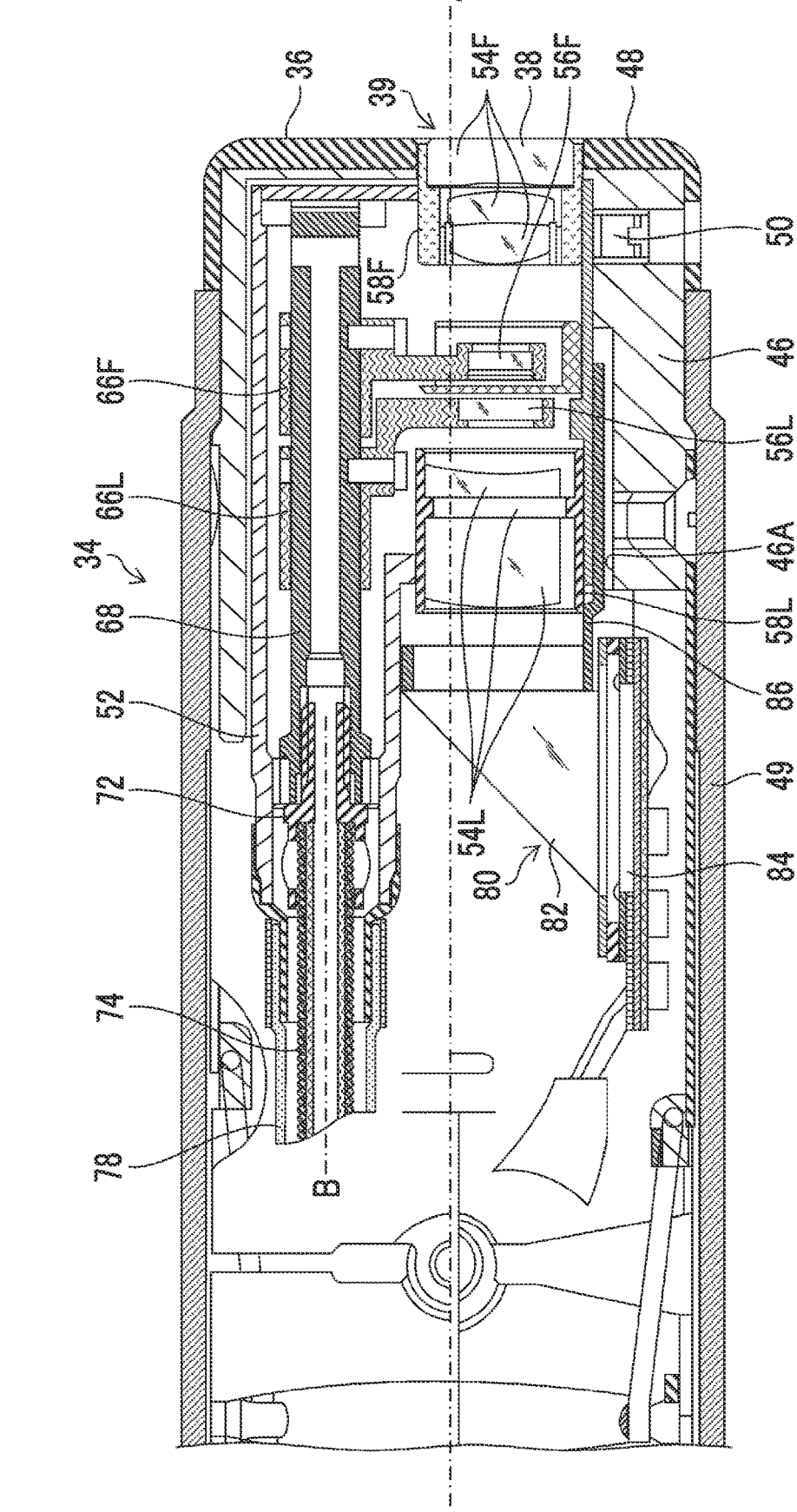
FIG. 3 is a vertical cross-sectional view of a distal end hard portion along a longitudinal axis of an insertion part.
Figure 4:
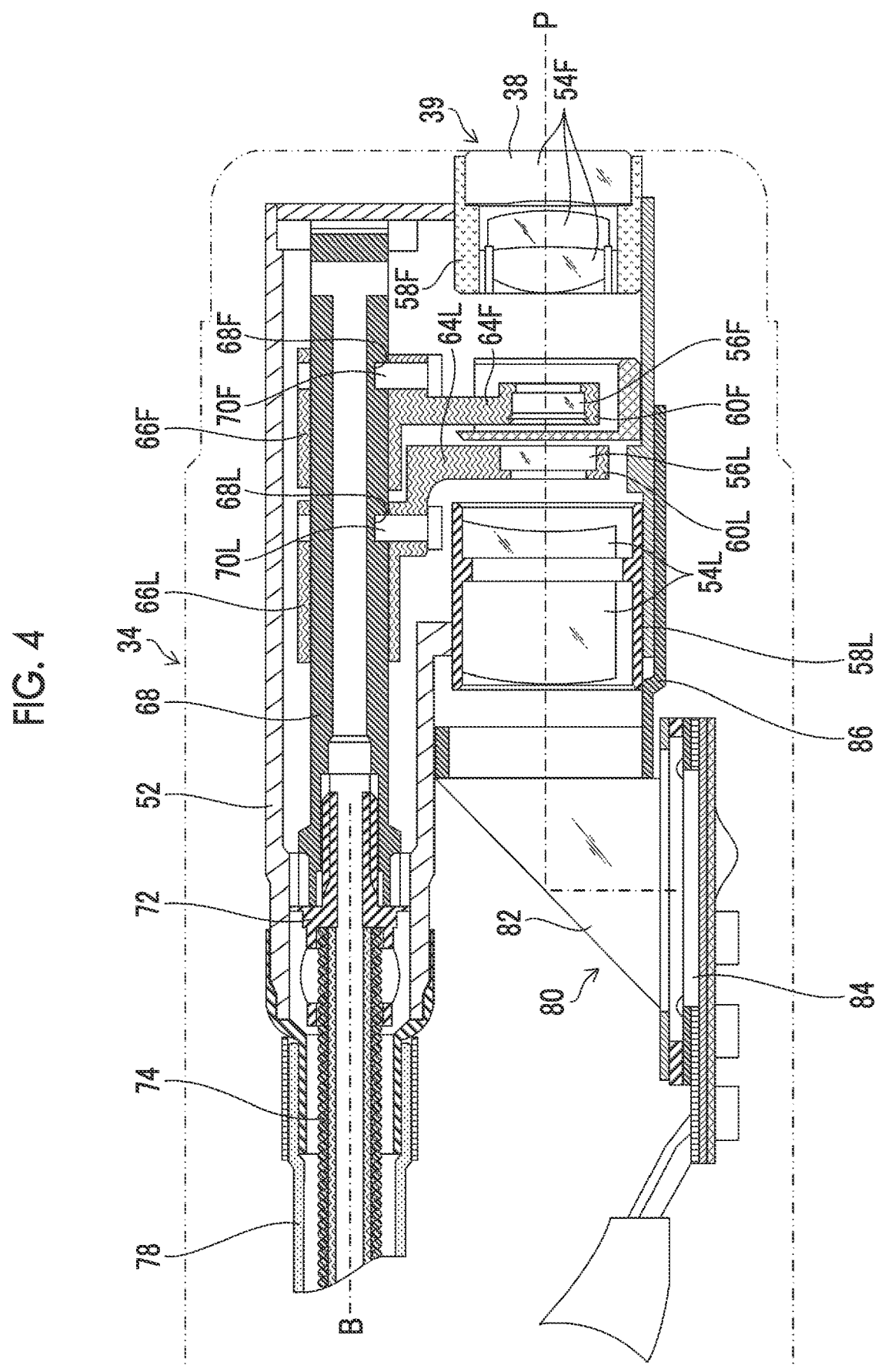
FIG. 4 is a vertical cross-sectional view of an observation optical system along the longitudinal axis of the insertion part.

Hereinafter, a configuration of an observation optical system 39 including the observation window 38 provided in the distal end hard portion 34 will be described. FIG. 3 is a vertical cross-sectional view of the distal end hard portion 34 along the longitudinal axis A. FIG. 4 is a vertical cross-sectional view of the observation optical system 39 along an optical axis P of the observation optical system 39. It should be noted that the longitudinal axis A and the optical axis P are parallel to each other.

As shown in FIG. 3, the observation window 38 is attached to a distal end part body 46. The distal end part body 46 is formed in a substantially cylindrical shape, and is formed with a through-hole 46A in a direction of the longitudinal axis A. The observation window 38 is inserted into the through-hole 46A from a base end side to a distal end side of the through-hole 46A, and then is fixed to the distal end part body 46 by a screw 50. It should be noted that, in the distal end hard portion 34, after the contents, such as the observation window 38, are fixed to the distal end part body 46, an outer peripheral surface of the distal end part body 46 is covered with an outer cover 49, and the distal end surface of the distal end part body 46 is equipped with a cap 48.

As shown in FIG. 4, the observation optical system 39 comprises stationary lens groups 54F and 54L and movable lens groups 56F and 56L, and these lens groups are accommodated in a housing 52. The stationary lens groups 54F and 54L and the movable lens groups 56F and 56L are each composed of one or several lenses.

The stationary lens groups 54F and 54L are mounted on stationary lens frames 58F and 58L, respectively, and are fixed to the housing 52 via the stationary lens frames 58F and 58L. The stationary lens frames 58F and 58L are disposed at intervals in a direction of the optical axis P shown in FIG. 4.

The movable lens groups 56F and 56L are disposed between the stationary lens group 54F and the stationary lens group 54L on the optical axis P and are held by movable lens frames 60F and 60L, respectively. Arms 64F and 64L are installed consecutively to the movable lens frames 60F and 60L, and ring parts 66F and 66L are formed at the distal ends of the arms 64F and 64L. A cam shaft 68 is inserted into the ring parts 66F and 66L, and the ring parts 66F and 66L are slidably supported by the cam shaft 68. In addition, cam pins 70F and 70L are projected on the ring parts 66F and 66L toward the inside of the ring parts 66F and 66L, and the cam pins 70F and 70L are engaged with cam grooves 68F and 68L spirally formed on an outer surface of the cam shaft 68. Therefore, by rotating the cam shaft 68 about an axial center of the cam shaft 68, the ring parts 66F and 66L move to the distal end side (right direction side in FIG. 4) or the base end side (left direction side in FIG. 4), and the movable lens groups 56F and 56L move forward and backward along the direction of the optical axis P. In this case, the movable lens groups 56F and 56L move in a direction close to or away from each other, whereby the focus adjustment or the zoom operation is performed. It should be noted that the lens configuration of the observation optical system 39 shown in FIGS. 3 and 4 is not limited to the embodiment described above, and for example, an embodiment may be adopted in which the stationary lens group may be composed of one group or the movable lens group may be composed of one group or three groups. The movable lens groups 56F and 56L of the present example are examples of a distal end optical system according to the embodiment of the present invention, and are provided on the distal end side of the insertion part 12.

In the cam shaft 68, the axial center of the cam shaft 68 is disposed parallel to the optical axis P of the observation optical system 39, and is supported by the housing 52 in a rotationally movable manner. A flexible shaft 74 is attached to a base end part of the cam shaft 68 via a linking tool 72.

The flexible shaft 74 has a shaft axis B, and is provided from the hand operating part 14 to the insertion part 12 in FIG. 1. The flexible shaft 74 is configured to rotate in a rotation direction about the shaft axis B by linking a distal end side with the cam shaft 68 via the linking tool 72 and linking a base end side with a linking tool 76 (see FIG. 5), which will be described below, as shown in FIG. 4. In a case in which the flexible shaft 74 rotates in the rotation direction described above, the cam shaft 68 is rotated about the axial center. As a result, the movable lens groups 56F and 56L are moved in the direction of the optical axis P, and the focus adjustment or the zoom operation is performed. The flexible shaft 74 of the present example is an example of a shaft according to the embodiment of the present invention, and is composed of a close contact coil spring as an example. It should be noted that an operation member or the like for rotationally operating the flexible shaft 74 will be described below.

As shown in FIG. 4, a distal end side of a protective tube 78 is fixed to a base end side of the housing 52. The flexible shaft 74 is protected by being inserted into the protective tube 78, and other contents (light guide, signal cable, air supply/water supply tube, and the like) contained in the insertion part 12 (see FIG. 1) are prevented from coming into contact with the flexible shaft 74. Similarly to the flexible shaft 74, the protective tube 78 is provided from the hand operating part 14 to the insertion part 12 of FIG. 1.

In addition, an imaging apparatus 80 is attached to the housing 52. The imaging apparatus 80 is disposed on the hand operating part 14 (see FIG. 1) side with respect to the stationary lens frame 58L. The imaging apparatus 80 mainly includes a prism 82 that bends an optical path of the observation optical system 39 by 90°, and a solid-state imaging element 84 that is disposed at an image-forming position of the observation optical system 39. The imaging apparatus 80 is attached to the observation optical system 39 by fixing a lens barrel holder 86, which is adhered to the prism 82, to the housing 52.

Hereinafter, some embodiments (first and second embodiments) of the zoom operation mechanism that rotates the flexible shaft 74 about the shaft axis B for performing the zoom operation will be described.

First Embodiment of Zoom Operation Mechanism

Figure 5:
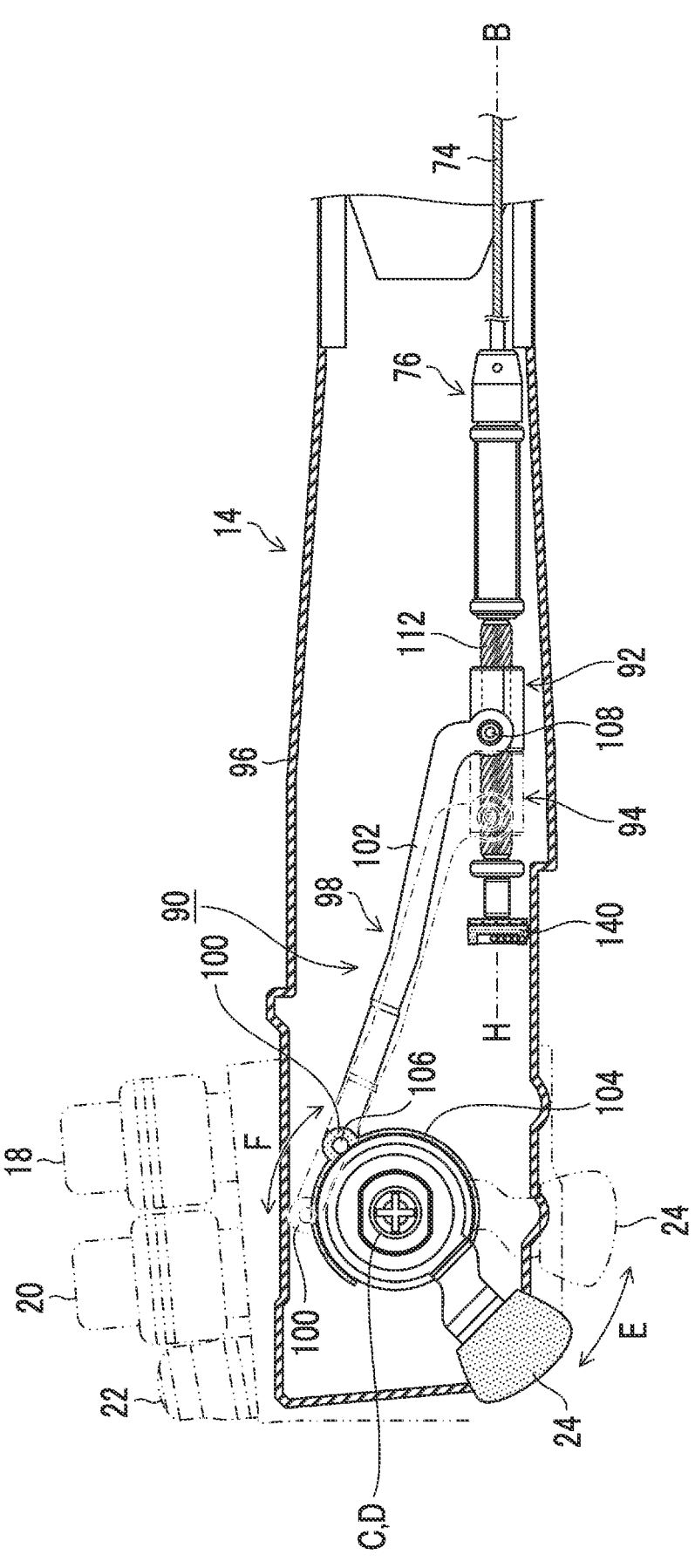
FIG. 5 is an explanatory diagram showing a configuration of a zoom operation mechanism according to a first embodiment.

FIG. 5 is an explanatory diagram showing a configuration of a zoom operation mechanism 90 according to the first embodiment. As shown in FIG. 5, the zoom operation mechanism 90 according to the first embodiment comprises a zoom operation knob 24, a slider 92, and a power conversion transmission mechanism 94. The zoom operation knob 24, the slider 92, and the power conversion transmission mechanism 94 are each provided in the hand operating part 14.

As shown in FIG. 1, the zoom operation knob 24 is provided to be exposed to the outside of the hand operating part 14, and is manually operated by an operator who operates the endoscope 10. The zoom operation knob 24 is configured to rotate by being rotatably supported by a frame 96 of the hand operating part 14 shown in FIG. 5. Further, as an example, a rotation axis C of the zoom operation knob 24 is disposed coaxially with a rotation axis D (see FIG. 5) of the bending operation knob 26 (see FIG. 1). With such a configuration, the zoom operation knob 24 can be easily operated with the finger of the operator who operates the bending operation knob 26. In addition, since the rotation axis C is shared with the rotation axis D, it is not necessary to separately provide the rotation axis C, so that the zoom operation mechanism 90 can be simplified. The zoom operation knob 24 is an example of an operation member according to the present invention, and is an example of a rotational operation member.

The slider 92 shown in FIG. 5 moves forward and backward in the direction of the shaft axis B according to the rotational operation of the zoom operation knob 24. Hereinafter, an example of a transmission mechanism 98 for transmitting a rotational operation force of the zoom operation knob 24 to the slider 92 will be described.

The transmission mechanism 98 of the present example includes a swing member 100 and a link member 102. The swing member 100 is a rotating ring 104 that is integrally configured with the zoom operation knob 24, and is configured as a protruding portion that protrudes from an outer peripheral portion of the rotating ring 104 that is rotatable about the rotation axis C. With such a configuration, in a case in which the zoom operation knob 24 is rotationally operated in a direction indicated by an arrow E in FIG. 5, the swing member 100 can swing in a direction of an arrow F about the rotation axis C. The swing member 100 is an example of a swing member according to the embodiment of the present invention.

The link member 102 links the swing member 100 with the slider 92. Specifically, in FIG. 5, a left end of the link member 102 is supported pivotally by the swing member 100 via a pin 106, and a right end of the link member 102 is supported pivotally by the slider 92 via a pin 108. With such a configuration, in a case in which the swing member 100 swings in a clockwise direction about the rotation axis C, the link member 102 can linearly move the slider 92 in a right direction in FIG. 5 in the direction of the shaft axis B. Further, in a case in which the swing member 100 swings in a counterclockwise direction about the rotation axis C, the link member 102 can linearly move the slider 92 in a left direction in FIG. 5 in the direction of the shaft axis B. As a result, the link member 102 functions as a member that moves the slider 92 forward and backward in the direction of the shaft axis B. The link member 102 is an example of a link member according to the embodiment of the present invention.

The power conversion transmission mechanism 94 shown in FIG. 5 rotates the flexible shaft 74 about the shaft axis B by the forward and backward movement of the slider 92. Hereinafter, a specific configuration of the power conversion transmission mechanism 94 will be described with reference to FIGS. 6 to 8.

Figure 6:
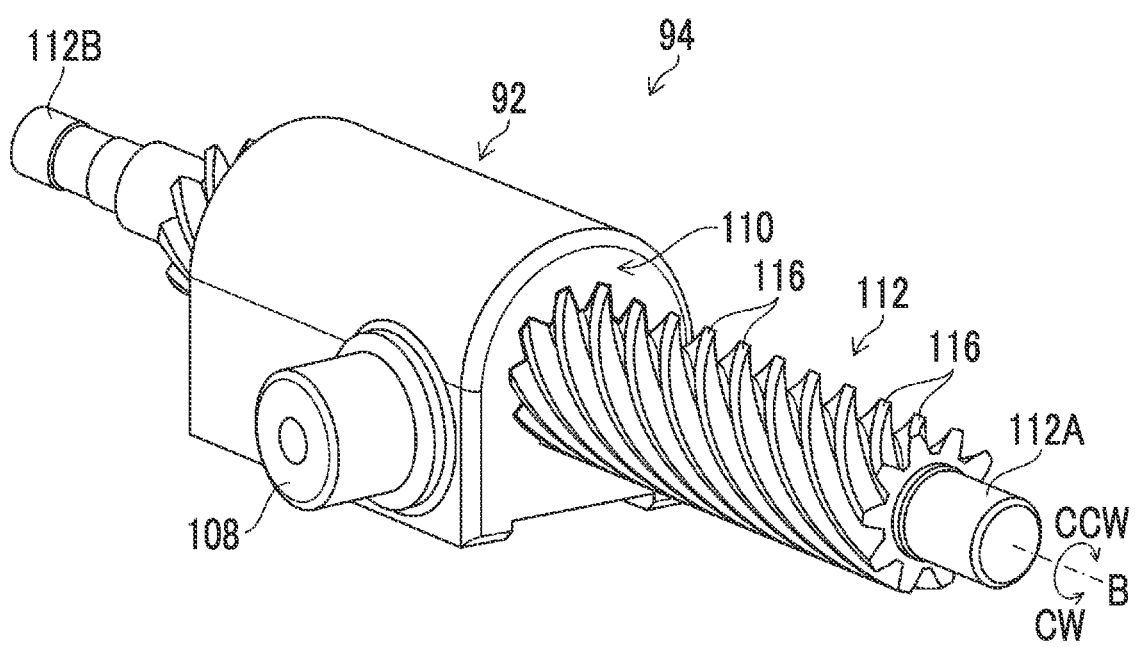
FIG. 6 is an overall perspective view of a power conversion transmission mechanism adopted in the first embodiment.
Figure 7:
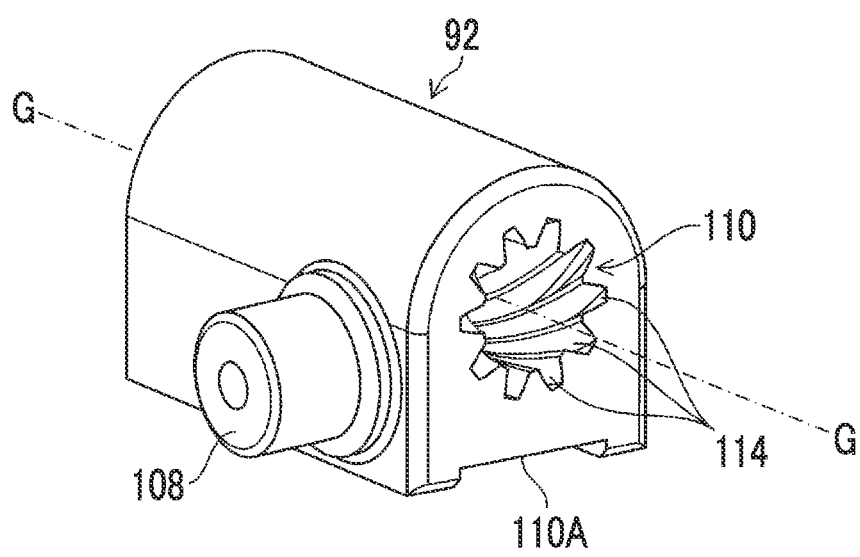
FIG. 7 is a perspective view of a nut which is one of components of the power conversion transmission mechanism shown in FIG. 6.
Figure 8:
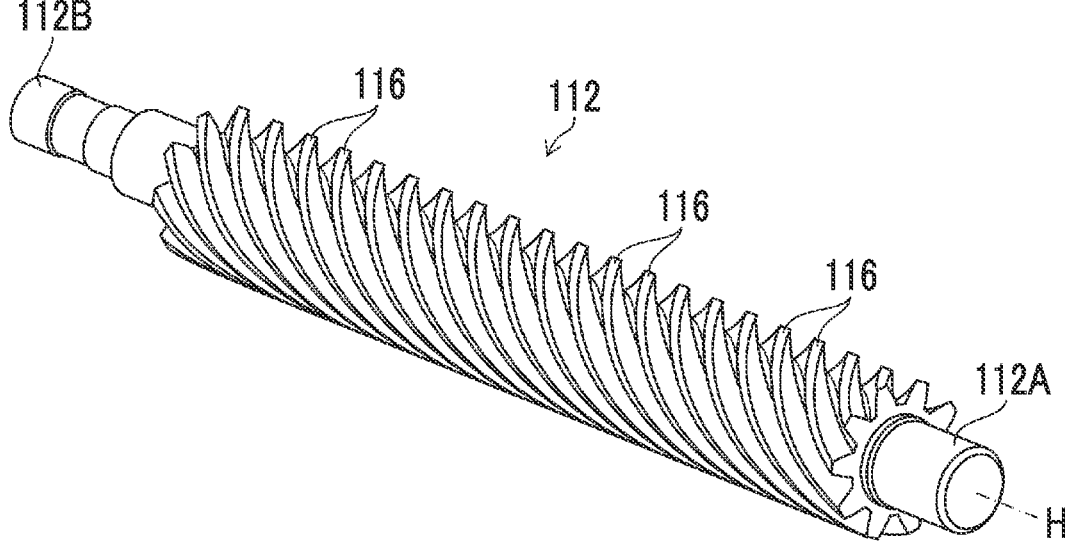
FIG. 8 is a perspective view of a screw shaft which is one of the components of the power conversion transmission mechanism shown in FIG. 6.

FIG. 6 is an overall perspective view of the power conversion transmission mechanism 94. FIG. 7 is a perspective view of a nut 110, which is one of components of the power conversion transmission mechanism 94. FIG. 8 is a perspective view of a screw shaft 112, which is one of the components of the power conversion transmission mechanism 94. As shown in FIGS. 6 to 8, the power conversion transmission mechanism 94 includes the nut 110 and the screw shaft 112.

As shown in FIG. 7, the nut 110 is provided on the slider 92. The nut 110 is configured as a substantially tubular body including a nut axis G and a female screw 114 is spirally formed on an inner peripheral surface thereof along a direction of the nut axis G. The nut 110 is an example of an engagement member according to the embodiment of the present invention. It should be noted that the slider 92 of the present example is configured as a substantially tubular body that covers an outer surface (excluding a flat bottom surface 110A of FIG. 7) of the nut 110.

As shown in FIG. 8, the screw shaft 112 is a shaft body having an axial center H, and a male screw 116 is spirally formed on an outer peripheral surface thereof along a direction of the axial center H. The male screw 116 and the female screw 114 of the nut 110 (see FIG. 7) are engaged (screwed) to configure the power conversion transmission mechanism 94 of the present example as shown in FIG. 6. The power conversion transmission mechanism 94 is an example of a power conversion transmission mechanism according to the embodiment of the present invention. The screw shaft 112 is an example of a shaft member according to the embodiment of the present invention, and the male screw 116 is an example of an engaged part according to the embodiment of the present invention.

As an example, the power conversion transmission mechanism 94 configured as described above is provided in the hand operating part 14 as follows. That is, as shown in FIG. 5, after the axial center H of the screw shaft 112 is disposed on an extension line of the shaft axis B of the flexible shaft 74, a distal end (right end 112A of FIG. 6) of the screw shaft 112 is linked with the base end of the flexible shaft 74 via the linking tool 76. Also, a base end (left end 112B in FIG. 6) of the screw shaft 112 is attached to the frame 96 via a bearing (not shown). As a result, the power conversion transmission mechanism 94 is provided in the hand operating part 14. Further, with the power conversion transmission mechanism 94 of the present example, in a case in which the slider 92 moves forward and backward by the rotational operation of the zoom operation knob 24, the nut 110 linearly moves with the forward and backward movement of the slider 92. Then, in a case in which the linear movement of the nut 110 is converted into the rotational movement by the female screw 114 and the male screw 116, the screw shaft 112 rotates in the rotation direction about the shaft axis B. As a result, the rotation of the screw shaft 112 is transmitted to the flexible shaft 74 via the linking tool 76, and the flexible shaft 74 rotates about the shaft axis B.

Hereinafter, an action of the zoom operation mechanism 90 according to the first embodiment will be described.

In a case in which the zoom operation knob 24 shown by a solid line in FIG. 5 is rotationally operated in a counterclockwise direction about the rotation axis C, the swing member 100 and the rotating ring 104 swing in a counterclockwise direction from the position shown by the solid line. As a result, the link member 102 linked with the swing member 100 is pulled by the swing member 100 and moves in the left direction in FIG. 5, and the slider 92 linked with the link member 102 moves in the left direction in FIG. 5.

Then, the nut 110 (see FIG. 6) linearly moves in the left direction with the movement of the slider 92 in the left direction. Then, the linear movement of the nut 110 in the left direction is converted into the rotational movement by the female screw 114 (see FIG. 7) of the nut 110 and the male screw 116 (see FIG. 8) of the screw shaft 112. As a result, the screw shaft 112 smoothly rotates in the rotation direction about the shaft axis B (for example, in a clockwise direction CW as the screw shaft 112 is viewed from the left end 112B in FIG. 6), the rotation of the screw shaft 112 is transmitted to the flexible shaft 74 via the linking tool 76, and the flexible shaft 74 rotates about the shaft axis B. As a result, by rotating the cam shaft 68 shown in FIG. 4, the movable lens groups 56F and 56L are moved in the direction of the optical axis P, and the zoom operation is performed, for example, on a wide side.

On the contrary, in a case in which the zoom operation knob 24 shown by a two-dot chain line in FIG. 5 is rotationally operated in a clockwise direction about the rotation axis C, the swing member 100 and the rotating ring 104 swing in a clockwise direction from the position shown by the two-dot chain line. As a result, the link member 102 linked with the swing member 100 is pushed by the swing member 100 and moves in the right direction in FIG. 5, and the slider 92 linked with the link member 102 moves in the right direction in FIG. 5.

Then, the nut 110 linearly moves in the right direction with the movement of the slider 92 in the right direction. Then, the linear movement of the nut 110 in the right direction is converted into the rotational movement by the female screw 114 (see FIG. 7) of the nut 110 and the male screw 116 (see FIG. 8) of the screw shaft 112. As a result, the screw shaft 112 smoothly rotates in the rotation direction about the shaft axis B (for example, in a counterclockwise direction CCW as the screw shaft 112 is viewed from the left end 112B in FIG. 6), the rotation of the screw shaft 112 is transmitted to the flexible shaft 74 via the linking tool 76, and the flexible shaft 74 rotates about the shaft axis B. As a result, by rotating the cam shaft 68 shown in FIG. 4, the movable lens groups 56F and 56L are moved in the direction of the optical axis P, and the zoom operation is performed, for example, on a telephoto side.

Therefore, with the zoom operation mechanism 90 of the first embodiment, since the configuration is adopted in which the slider 92 is moved forward and backward in the direction of the shaft axis B according to the rotational operation of the zoom operation knob 24, and the flexible shaft 74 is rotated by the power conversion transmission mechanism 94 by the forward and backward movement of the slider 92, the movable lens groups 56F and 56L can be efficiently moved forward and backward in the direction of the optical axis P. In addition, since the feed screw mechanism including the nut 110 and the screw shaft 112 is adopted as the power conversion transmission mechanism 94, the linear movement of the slider 92 can be effectively converted into the rotational movement.

Second Embodiment of Zoom Operation Mechanism

Figure 9:
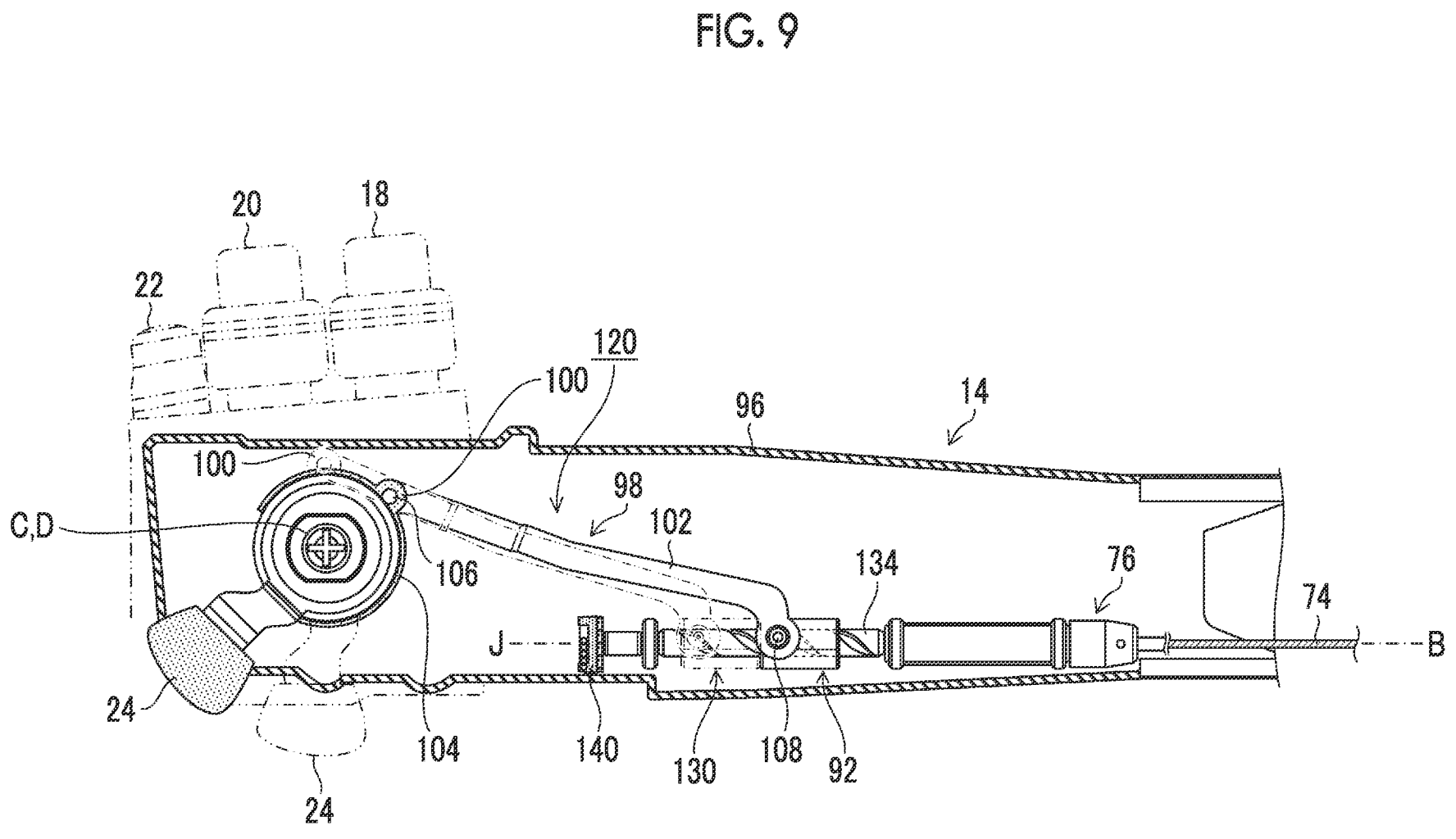

FIG. 9 is an explanatory diagram showing a configuration of a zoom operation mechanism 120 according to the second embodiment.

Here, a difference in configuration between the second embodiment shown in FIG. 9 and the first embodiment shown in FIG. 5 will be described. The feed screw mechanism including the nut 110 and the screw shaft 112 is adopted as the power conversion transmission mechanism 94 of the first embodiment, whereas a cam mechanism including a cam pin 132 (see FIG. 11) and a cam shaft 134 is adopted as a power conversion transmission mechanism 130 of the second embodiment shown in FIG. 9. Since the other configurations (zoom operation knob 24, slider 92, swing member 100, and link member 102) are the same, in the description of the zoom operation mechanism 120 of the second embodiment, the power conversion transmission mechanism 130 shown in FIGS. 10 to 12 will be mainly described.

Figure 10:
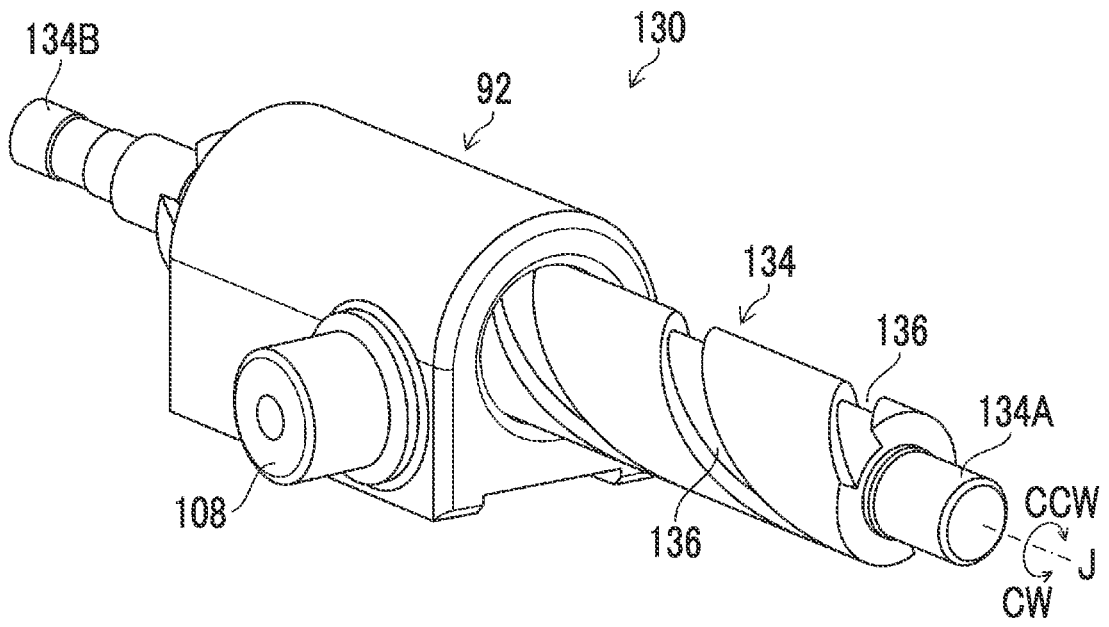
FIG. 10 is an overall perspective view of a power conversion transmission mechanism adopted in the second embodiment.
Figure 11:
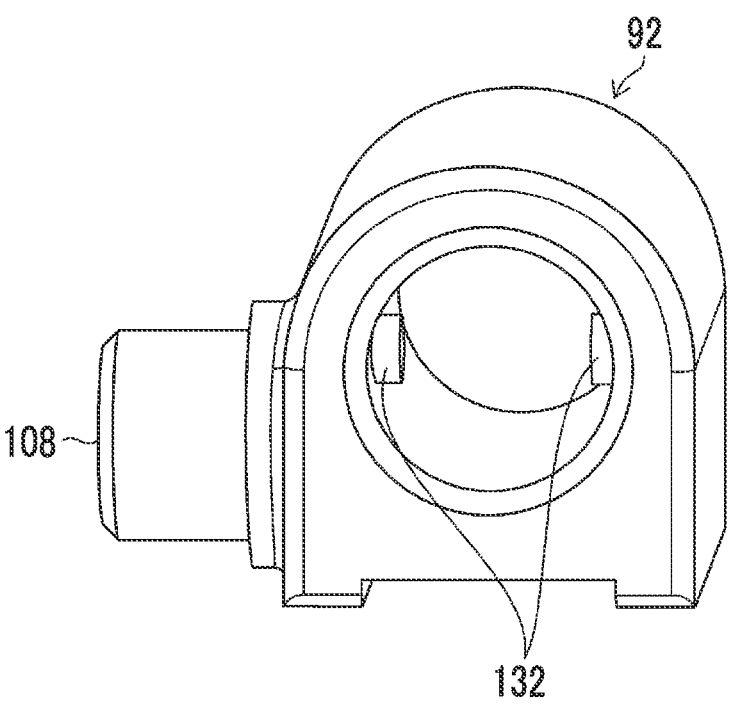
FIG. 11 is a perspective view of a cam pin which is a component of the power conversion transmission mechanism shown in FIG. 10.
Figure 12:
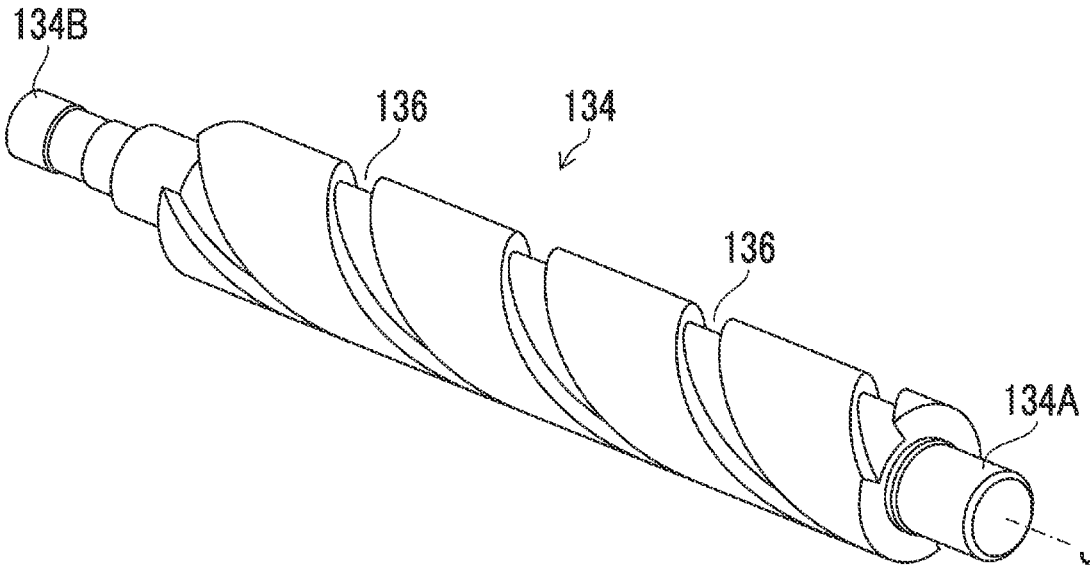
FIG. 12 is a perspective view of a cam shaft which is a component of the power conversion transmission mechanism shown in FIG. 10.

FIG. 10 is an overall perspective view of the power conversion transmission mechanism 130. FIG. 11 is a perspective view of a pair of cam pins 132 which are one of the components of the power conversion transmission mechanism 130. FIG. 12 is a perspective view of the cam shaft 134, which is one of the components of the power conversion transmission mechanism 130. As shown in FIGS. 10 to 12, the power conversion transmission mechanism 130 includes the pair of cam pins 132 and the cam shaft 134.

As shown in FIG. 11, the slider 92 is formed in a tubular shape, and the pair of cam pins 132 are projected from the inner peripheral surface of the slider 92 to face each other. The cam pin 132 is an example of an engagement member according to the embodiment of the present invention.

As shown in FIG. 12, the cam shaft 134 is a shaft body having an axial center J, and a cam groove 136 is spirally formed on an outer peripheral surface thereof along a direction of the axial center J. The cam groove 136 and the pair of cam pins 132 (see FIG. 11) are engaged with each other to configure the power conversion transmission mechanism 130 of the present example as shown in FIG. 10. The power conversion transmission mechanism 130 is an example of a power conversion transmission mechanism according to the embodiment of the present invention. The cam shaft 134 is an example of a shaft member according to the embodiment of the present invention, and the cam groove 136 is an example of an engaged part according to the embodiment of the present invention.

As an example, the power conversion transmission mechanism 130 configured as described above is provided in the hand operating part 14 as follows. That is, as shown in FIG. 9, after the axial center J of the cam shaft 134 is disposed on an extension line of the shaft axis B of the flexible shaft 74, a distal end (right end 134A of FIG. 10) of the cam shaft 134 is linked with the base end of the flexible shaft 74 via the linking tool 76. Also, a base end of the cam shaft 134 (left end 134B in FIG. 10) is attached to the frame 96 via a bearing (not shown). As a result, the power conversion transmission mechanism 130 is provided in the hand operating part 14. Further, with the power conversion transmission mechanism 130 of the present example, in a case in which the slider 92 moves forward and backward by the rotational operation of the zoom operation knob 24, the pair of cam pins 132 linearly move with the forward and backward movement of the slider 92. Further, in a case in which the linear movement of the pair of cam pins 132 is converted into the rotational movement by the cam groove 136, the cam shaft 134 rotates in the rotation direction about the shaft axis B. As a result, the rotation of the cam shaft 134 is transmitted to the flexible shaft 74 via the linking tool 76, and the flexible shaft 74 rotates about the shaft axis B.

Hereinafter, an action of the zoom operation mechanism 120 according to the second embodiment will be described. It should be noted that a point that overlaps with the action of the zoom operation mechanism 90 of the first embodiment will be described repeatedly.

In a case in which the zoom operation knob 24 shown by a solid line in FIG. 9 is rotationally operated in a counterclockwise direction about the rotation axis C, the swing member 100 and the rotating ring 104 swing in a counterclockwise direction from the position shown by the solid line. As a result, the link member 102 linked with the swing member 100 is pulled by the swing member 100 and moves in the left direction in FIG. 9, and the slider 92 linked with the link member 102 moves in the left direction in FIG. 9.

Then, the pair of cam pins 132 linearly move in the left direction with the movement of the slider 92 in the left direction. Then, the linear movement of the pair of cam pins 132 in the left direction is converted into the rotational movement by the cam groove 136 (see FIG. 12) of the cam shaft 134. As a result, the cam shaft 134 smoothly rotates in the rotation direction about the shaft axis B (for example, in the clockwise direction CW as the cam shaft 134 is viewed from the left end 134B in FIG. 10), the rotation of the cam shaft 134 is transmitted to the flexible shaft 74 via the linking tool 76, and the flexible shaft 74 rotates about the shaft axis B. As a result, by rotating the cam shaft 68 shown in FIG. 4, the movable lens groups 56F and 56L are moved in the direction of the optical axis P, and the zoom operation is performed, for example, on the wide side.

On the contrary, in a case in which the zoom operation knob 24 shown by a two-dot chain line in FIG. 9 is rotationally operated in a clockwise direction about the rotation axis C, the swing member 100 and the rotating ring 104 swing in a clockwise direction from the position shown by the two-dot chain line. As a result, the link member 102 linked with the swing member 100 is pushed by the swing member 100 and moves in the right direction in FIG. 9, and the slider 92 linked with the link member 102 moves in the right direction in FIG. 9.

Then, the pair of cam pins 132 linearly move in the right direction with the movement of the slider 92 in the right direction. Then, the linear movement of the pair of cam pins 132 in the right direction is converted into the rotational movement by the cam groove 136 (see FIG. 12) of the cam shaft 134. As a result, the cam shaft 134 smoothly rotates in the rotation direction about the shaft axis B (for example, in the counterclockwise direction CCW as the cam shaft 134 is viewed from the left end 135B in FIG. 10), the rotation of the cam shaft 134 is transmitted to the flexible shaft 74 via the linking tool 76, and the flexible shaft 74 rotates about the shaft axis B. As a result, by rotating the cam shaft 68 shown in FIG. 4, the movable lens groups 56F and 56L are moved in the direction of the optical axis P, and the zoom operation is performed, for example, on the telephoto side.

Therefore, with the zoom operation mechanism 120 of the second embodiment, since the configuration is adopted in which the slider 92 is moved forward and backward in the direction of the shaft axis B according to the rotational operation of the zoom operation knob 24, and the flexible shaft 74 is rotated by the power conversion transmission mechanism 130 by the forward and backward movement of the slider 92, the movable lens groups 56F and 56L can be efficiently moved forward and backward in the direction of the optical axis P. Further, since the cam mechanism including the pair of cam pins 132 and the cam shaft 134 is adopted as the power conversion transmission mechanism 130, the linear movement of the slider 92 can be effectively converted into the rotational movement.

Rotary Encoder

Here, a rotary encoder 140 is also provided in the first embodiment shown in FIG. 5 and the second embodiment shown in FIG. 9. The rotary encoder 140 detects a rotation angle of the flexible shaft 74, is linked with the left end 112B (see FIG. 6) of the screw shaft 112 as an example in the first embodiment of FIG. 5, and is linked with the left end 134B (see FIG. 10) of the cam shaft 134 as an example in the second embodiment of FIG. 9. The rotary encoder 140 is an example of a rotation detection unit according to the embodiment of the present invention.

Figure 13:
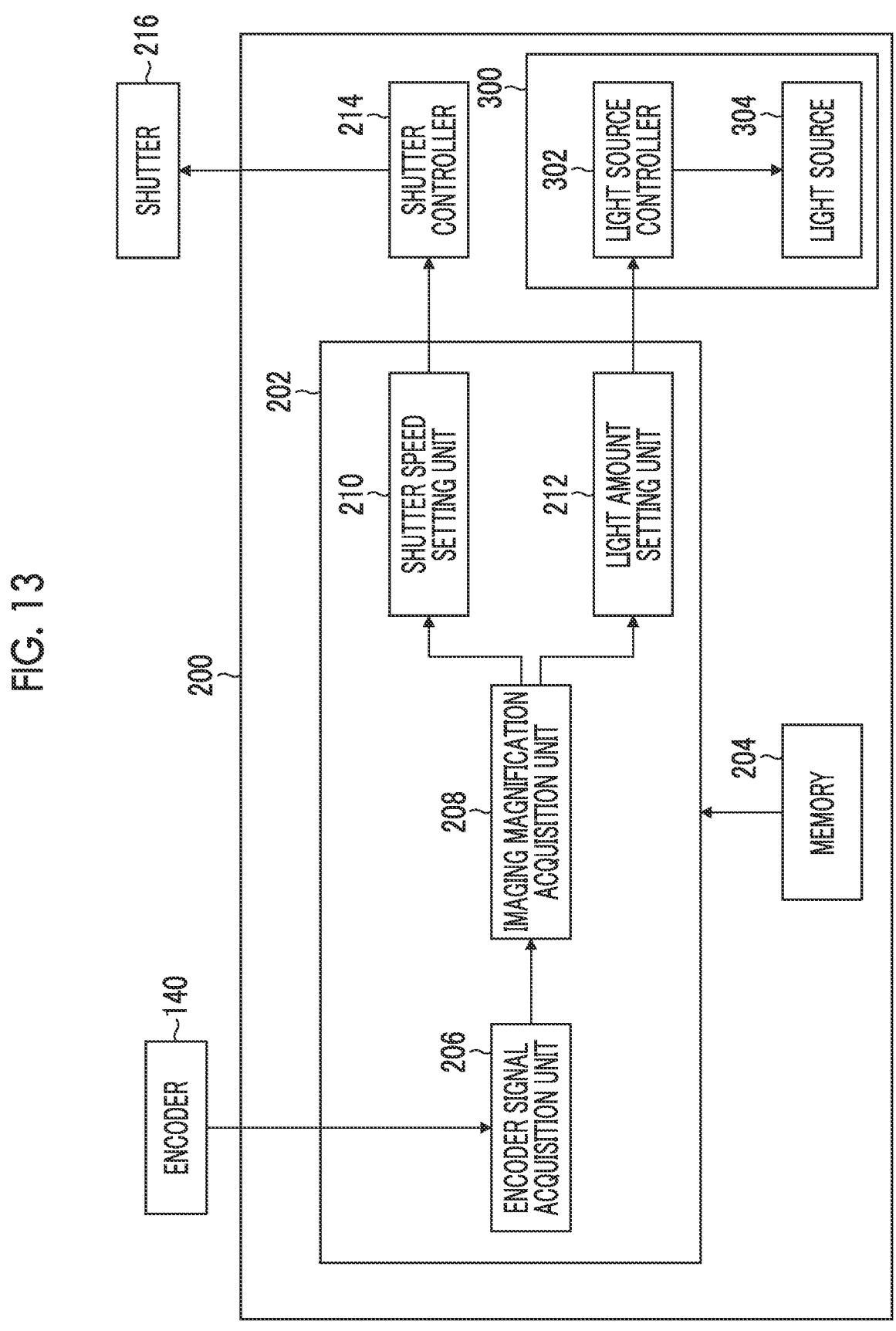
FIG. 13 is a functional block diagram showing a configuration of a processor device shown in FIG. 1.

A detection signal output from the rotary encoder 140 is input to the processor device 200 (see FIG. 1) of the endoscope 10 as an example. FIG. 13 is a functional block diagram showing a configuration of the processor device 200. The processor device 200 comprises a processor 202 and a memory 204.

As shown in FIG. 13, the processor 202 includes an encoder signal acquisition unit 206 that acquires the detection signal output from the rotary encoder 140, an imaging magnification acquisition unit 208 that acquires information indicating an imaging magnification corresponding to the detection signal acquired by the encoder signal acquisition unit 206 from the memory 204, a shutter speed setting unit 210 that sets a shutter speed corresponding to the imaging magnification acquired by the imaging magnification acquisition unit 208, and a light amount setting unit 212 that sets a light amount corresponding to the imaging magnification acquired by the imaging magnification acquisition unit 208.

The shutter speed setting unit 210 sets the shutter speed corresponding to the imaging magnification to a shutter controller 214, and the shutter controller 214 controls a shutter 216 at the set shutter speed. In addition, the light amount setting unit 212 sets the light amount corresponding to the imaging magnification to a light source controller 302 of the light source device 300, and the light source controller 302 controls the light source 304 with the set light amount.

The processor 202 executes a command stored in the memory 204. A hardware structure of the processor 202 is various processors as described below. Various processors include a central processing unit (CPU) as a general-purpose processor which acts as various function units by executing software (program), a graphics processing unit (GPU) as a processor specialized in image processing, a programmable logic device (PLD) as a processor of which a circuit configuration can be changed after manufacture, such as a field programmable gate array (FPGA), a dedicated electric circuit as a processor which has a circuit configuration specifically designed to execute specific processing, such as an application specific integrated circuit (ASIC), and the like.

One processing unit may be configured by using one of these various processors, or two or more processors of the same type or different types (for example, a plurality of FPGAs, or a combination of a CPU and an FPGA, or a combination of a CPU and a GPU). Moreover, a plurality of function units may be configured by using one processor. As a first example in which the plurality of function units are configured by using one processor, as represented by a computer such as a client or a server, there is a form in which one processor is configured by using a combination of one or more CPUs and software, and this processor acts as the plurality of function units. As a second example thereof, as represented by a system on chip (SoC), there is a form in which a processor, which implements the functions of the entire system including the plurality of function units by one integrated circuit (IC) chip, is used. As described above, various function units are configured by using one or more of the various processors described above as the hardware structure.

Further, the hardware structures of these various processors are, more specifically, an electric circuit (circuitry) in which circuit elements such as semiconductor elements are combined.

Figure 14:
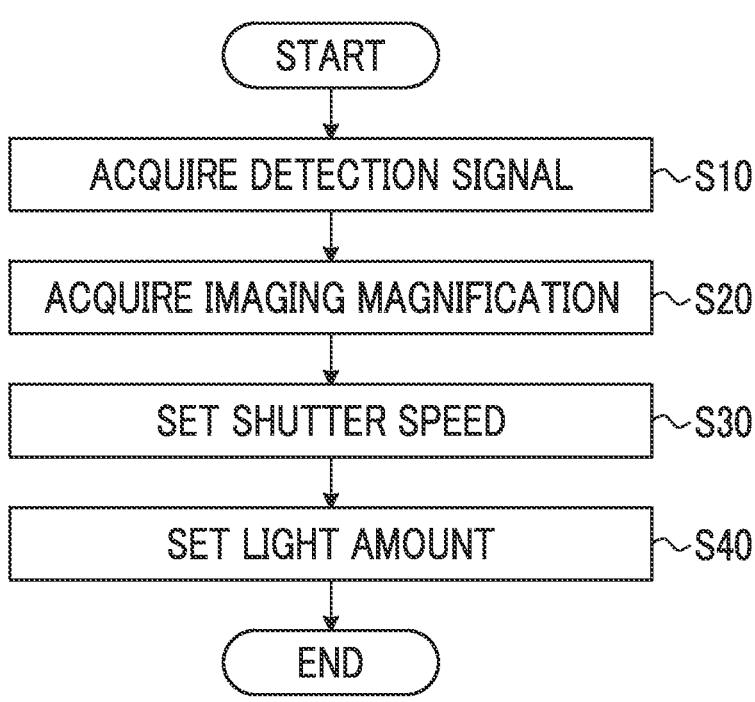
FIG. 14 is a flowchart showing a flow of processing by a processor.

FIG. 14 is a flowchart showing a flow of processing of setting the shutter speed and setting the light amount by the processor 202 shown in FIG. 13. As shown in FIG. 14, in step S10, the encoder signal acquisition unit 206 (see FIG. 13) acquires the detection signal from the rotary encoder 140 (see FIG. 13). Next, in step S20, the imaging magnification acquisition unit 208 (see FIG. 13) acquires the information indicating the imaging magnification corresponding to the detection signal acquired by the encoder signal acquisition unit 206 (see FIG. 13) from the memory 204. Then, in step S30, the shutter speed setting unit 210 (see FIG. 13) sets the shutter speed corresponding to the imaging magnification acquired by the imaging magnification acquisition unit 208 (see FIG. 13). Then, in step 40, the light amount setting unit 212 (see FIG. 13) sets the light amount corresponding to the imaging magnification acquired by the imaging magnification acquisition unit 208 (see FIG. 13). The above description is the flow of processing of setting the shutter speed and setting the light amount by the processor 202. It should be noted that step S30 and step S40 may be processed in parallel or may be processed in a different order.

The processing of the processor 202 will be briefly described. Since the image blur is likely to occur in a case in which the imaging magnification is increased by the zoom operation, the processor 202 sets the shutter speed to high speed, and sets the light amount for obtaining a sufficient light amount even at the shutter speed. As a result, it is possible to suppress image blur in a case in which the imaging magnification is increased.

Modification Example

Hereinafter, a modification example according to the "shaft" and the "operation member" which are the configuration requirements of the present invention will be described.

Shaft

As the shaft, the flexible shaft 74 having a flexibility is described as an example in the embodiment, but the present invention is not limited to this. For example, a rigid (non-flexible) shaft may be applied as the shaft. In this case, the rigid shaft can be applied to a rigid mirror in which the insertion part is composed of a hard member.

Operation Member

As the operation member, the zoom operation knob 24 configured to rotate is described as an example in the embodiment, but the present invention is not limited to this. For example, an operation member configured to linearly move may be applied. Specifically, a configuration may be adopted in which a knob member corresponding to the operation member is directly linked with the slider 92, and the knob member is linearly moved to move the slider 92 forward and backward. In this case, the zoom operation knob 24 and the transmission mechanism 98 (swing member 100 and link member 102) shown in FIGS. 5 and 9 are not required. However, from the viewpoint that the operation member can be easily operated with the finger of the operator who operates the bending operation knob 26 (see FIG. 1), it is preferable to adopt the configurations of the first embodiment (see FIG. 5) and the second embodiment (see FIG. 9) in which the zoom operation knob 24 and the transmission mechanism 98 are provided.

Although the endoscope according to the embodiment is described above, the present invention may be improved or modified in some ways without departing from the gist of the present invention.

EXPLANATION OF REFERENCES

10: endoscope
12: insertion part
14: hand operating part
16: universal cable
18: air supply/water supply button
20: suction button
22: shutter button
24: zoom operation knob
26: bending operation knob
28: forceps insertion part
30: soft portion
32: bendable portion
34: distal end hard portion
36: distal end surface
38: observation window
39: observation optical system
40A: illumination window
40B: illumination window
42: air supply/water supply nozzle
44: forceps port
46: distal end part body
46A: through-hole
48: cap
49: outer cover
50: screw
52: housing
54F: stationary lens group
54L: stationary lens group
56F: movable lens group
56L: movable lens group
58F: stationary lens frame
58L: stationary lens frame
60F: movable lens frame
60L: movable lens frame
64F: arm
64L: arm
66: cam shaft
66F: ring part
66L: ring part
68F: cam groove
68L: cam groove
70F: cam pin
70L: cam pin
72: linking tool
74: flexible shaft
76: linking tool
78: protective tube
80: imaging apparatus
82: prism
84: solid-state imaging element
86: lens barrel holder
90: zoom operation mechanism
92: slider
94: power conversion transmission mechanism
96: frame
98: transmission mechanism

100: swing member
102: link member
104: rotating ring
106: pin
108: pin
110: nut
110A: bottom surface
112: screw shaft
112A: right end
112B: left end
114: female screw
115: female screw
116: male screw
120: zoom operation mechanism
130: power conversion transmission mechanism
132: cam pin
134: cam shaft
134A: right end
134B: left end
136: cam groove
200: processor device
202: processor
204: memory
206: encoder signal acquisition unit
208: imaging magnification acquisition unit
210: shutter speed setting unit
212: light amount setting unit
214: shutter controller
216: shutter
300: light source device
302: light source controller
304: light source
400: image processing device
A: longitudinal axis
B: shaft axis

What is claimed is:

1. An endoscope comprising:
a distal end optical system that is movable forward and backward in an optical axis direction;
a shaft that has a shaft axis, is configured to rotate in a rotation direction about the shaft axis, and moves the distal end optical system in the optical axis direction in a case in which the shaft rotates in the rotation direction;
a knob;
a slider that moves forward and backward in a direction of the shaft axis according to a rotating operation of the knob; and
a power conversion transmission mechanism that rotates the shaft by the forward and backward movement of the slider, wherein
the power conversion transmission mechanism includes
an engagement member comprising a nut or a cam pin provided on the slider, and
a shaft member that is linked with the shaft and is formed with a spiral engaged part, on an outer peripheral surface, with which the engagement member is engaged, and
the shaft member rotates the shaft by linear movement of the engagement member accompanied by the forward and backward movement of the slider.

2. The endoscope according to claim 1,
wherein the knob is a rotational operation member configured to be rotationally operated, and
the endoscope further comprises:

a swing member that swings in a case in which the rotational operation member is rotationally operated; and a link member that links the swing member with the slider and moves the slider forward and backward in the direction of the shaft axis in a case in which the swing member swings.

3. The endoscope according to claim 1, wherein the engagement member is a nut including a female screw, and the shaft member is a screw shaft including a male screw which is the engaged part.

4. The endoscope according to claim 1, wherein the engagement member is a cam pin, and the shaft member is a cam shaft including a cam groove which is the engaged part.

5. The endoscope according to claim 1, further comprising:

a rotary encoder that detects a rotation angle of the shaft.

6. The endoscope according to claim 1, further comprising:

an insertion part; and a hand operating part that is connected to a base end side of the insertion part, wherein the knob, the slider, and the power conversion transmission mechanism are provided on the hand operating part, the shaft is provided from the hand operating part to the insertion part, and the distal end optical system is provided on a distal end side of the insertion part.

7. The endoscope according to claim 6, wherein the knob is a rotational operation member configured to be rotationally operated, a bending operation knob that performs a bending operation of the insertion part is provided to be rotationally operated, on the hand operating part, and a rotation axis of the rotational operation member is disposed coaxially with a rotation axis of the bending operation knob.

\*    \*    \*    \*    \*